US010232149B2

(12) United States Patent
Lentz

(10) Patent No.: US 10,232,149 B2
(45) Date of Patent: *Mar. 19, 2019

(54) INTRODUCER ASSEMBLY EXTENSION AND METHOD OF USE

(71) Applicant: Cook Medical Technologies LLC, Bloomington, IN (US)

(72) Inventor: David Christian Lentz, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 162 days.

This patent is subject to a terminal disclaimer.

(21) Appl. No.: 15/350,771

(22) Filed: Nov. 14, 2016

(65) Prior Publication Data

US 2017/0056627 A1 Mar. 2, 2017

Related U.S. Application Data

(63) Continuation of application No. 14/155,780, filed on Jan. 15, 2014, now Pat. No. 9,526,872, which is a
(Continued)

(51) Int. Cl.
*A61M 25/00* (2006.01)
*A61M 25/01* (2006.01)
(Continued)

(52) U.S. Cl.
CPC ............ *A61M 25/104* (2013.01); *A61B 6/12* (2013.01); *A61B 6/487* (2013.01); *A61B 50/30* (2016.02);
(Continued)

(58) Field of Classification Search
CPC .......... A61M 25/0662; A61M 25/0905; A61M 25/104; A61M 25/002; A61M 2025/0681;
(Continued)

(56) References Cited

U.S. PATENT DOCUMENTS 3,782,381 A 1/1974 Winnie
3,856,009 A 12/1974 Winnie
(Continued)

OTHER PUBLICATIONS

Cook Medical, Micropuncture Introducer Set, p. 1, Published on World Wide Web at http://www.cookmedical.com/di/dataSheet.do?id=4622, prior to Jan. 5, 2010.
(Continued)

*Primary Examiner* — Katrina M Stransky
(74) *Attorney, Agent, or Firm* — Liell & McNeil

(57) ABSTRACT

An introducer set includes an introducer and dilator along with an extension in a sealed sterile peal open package. The extension is available for use during procedures where the puncture access site to the patient is close enough to the site to be treated in the patient that the physician's hands and/or head may be positioned in the fluroscopic area while the physician is attempting to maneuver a wire guide to a desired location. When the extension is attached to the introducer, the physician may perform a procedure, such as an antigrade stick in the lower leg of a patient, while maintaining their hands and head outside of the fluroscopic area while direct radiation is being supplied and the wire guide is being maneuvered to a desired treatment location. After the wire guide has been properly positioned and the radiation has been terminated, the extension may be disconnected from the introducer and the remaining portions of the procedure (guide catheter insertion, balloon catheter insertion and dilation, etc.) may proceed in a known manner. The extension need only be in the range of ten to thirty centimeters to allow the physician to work a safe distance from the fluroscopic area undergoing direct radiation.

12 Claims, 2 Drawing Sheets

Related U.S. Application Data continuation-in-part of application No. 12/725,787, filed on Mar. 17, 2010, now abandoned.

(51) Int. Cl.

| | | |
|---|---|---|
| *A61M 25/06* | (2006.01) | |
| *A61M 25/09* | (2006.01) | |
| *A61M 25/10* | (2013.01) | |
| *A61M 29/02* | (2006.01) | |
| *A61B 6/00* | (2006.01) | |
| *A61B 6/12* | (2006.01) | |
| *A61B 50/30* | (2016.01) | |
| *A61B 50/00* | (2016.01) | |

(52) U.S. Cl.
CPC ...... *A61M 25/002* (2013.01); *A61M 25/0108* (2013.01); *A61M 25/0662* (2013.01); *A61M 25/0905* (2013.01); *A61M 29/02* (2013.01); *A61B 6/481* (2013.01); *A61B 6/486* (2013.01); *A61B 2050/0065* (2016.02)

(58) Field of Classification Search
CPC ......... A61B 6/487; A61B 6/481; A61B 6/486; A61B 17/3415; A61B 17/3421; A61B 17/3417; A61B 2017/3445; A61B 6/12
See application file for complete search history.

(56) References Cited

U.S. PATENT DOCUMENTS

| | | | |
|---|---|---|---|
| 4,619,643 A | 10/1986 | Bai | |
| 4,973,313 A | 11/1990 | Katsaros et al. | |
| 5,234,406 A | 8/1993 | Drasner et al. | |
| 5,250,038 A | 10/1993 | Melker et al. | |
| 5,368,574 A | 11/1994 | Antonacci et al. | |
| 5,382,241 A | 1/1995 | Choudhury et al. | |
| 5,439,455 A | 8/1995 | Kieturakis et al. | |
| 5,512,052 A | 4/1996 | Jesch | |
| 5,935,110 A | 8/1999 | Brimhall | |
| 6,298,256 B1 | 10/2001 | Meyer | |
| 7,503,596 B2 | 3/2009 | Rome et al. | |
| 9,526,872 B2 * | 12/2016 | Lentz | A61B 6/12 |
| 2003/0097082 A1 | 5/2003 | Purdy et al. | |
| 2005/0043709 A1 | 2/2005 | Brimhall et al. | |
| 2005/0096585 A1 | 5/2005 | Schon et al. | |
| 2006/0142737 A1 * | 6/2006 | Tanghoj | A61M 25/002 |
| | | | 604/544 |
| 2007/0276354 A1 | 11/2007 | Osborne | |
| 2008/0058595 A1 | 3/2008 | Snoke et al. | |
| 2008/0171973 A1 | 7/2008 | House | |
| 2008/0243165 A1 | 10/2008 | Mauch et al. | |
| 2009/0131886 A1 | 5/2009 | Liu et al. | |
| 2010/0160863 A1 | 6/2010 | Heuser | |

OTHER PUBLICATIONS

Cook Medical, Slip-Cath Beacon Tip Catheters, p. 1, Published on World Wide Web at http://www.cookmedical.com/di/dataSheet.do?id=4744, prior to Jan. 5, 2010.

Cook Medical, Flexor Tuohy-Borst Sidearm Introducers, p. 1, Published on World Wide Web at http://www.cookmedical.com/di/dataSheet.do?id=4716, prior to Jan. 5, 2010.

Thermal Angel, Thermal Angel 9 Inch IV Extension Set, p. 1, Published on World Wide Web at http://www.thermalangel.com/html/products/catalog/ta-9ext-9-inch-iv-extension.html, prior to Jan. 22, 2010.

Wolf Medical Supply, Inc., Medex Microbore Extension Sets, Alaris IV Extension Sets, p. 1, Published on World Wide Web at http://www.wolfmed.com/products_wolfpak_ivextsets.htm, prior to Jan. 22, 2010.

Abbott I.V., Extension Set With Injection Port From Emergency Medical Products, p. 1, Published on World Wide Web at http://www.buyemp.com/product/1120409.html, prior to Jan. 22, 2010.

* cited by examiner

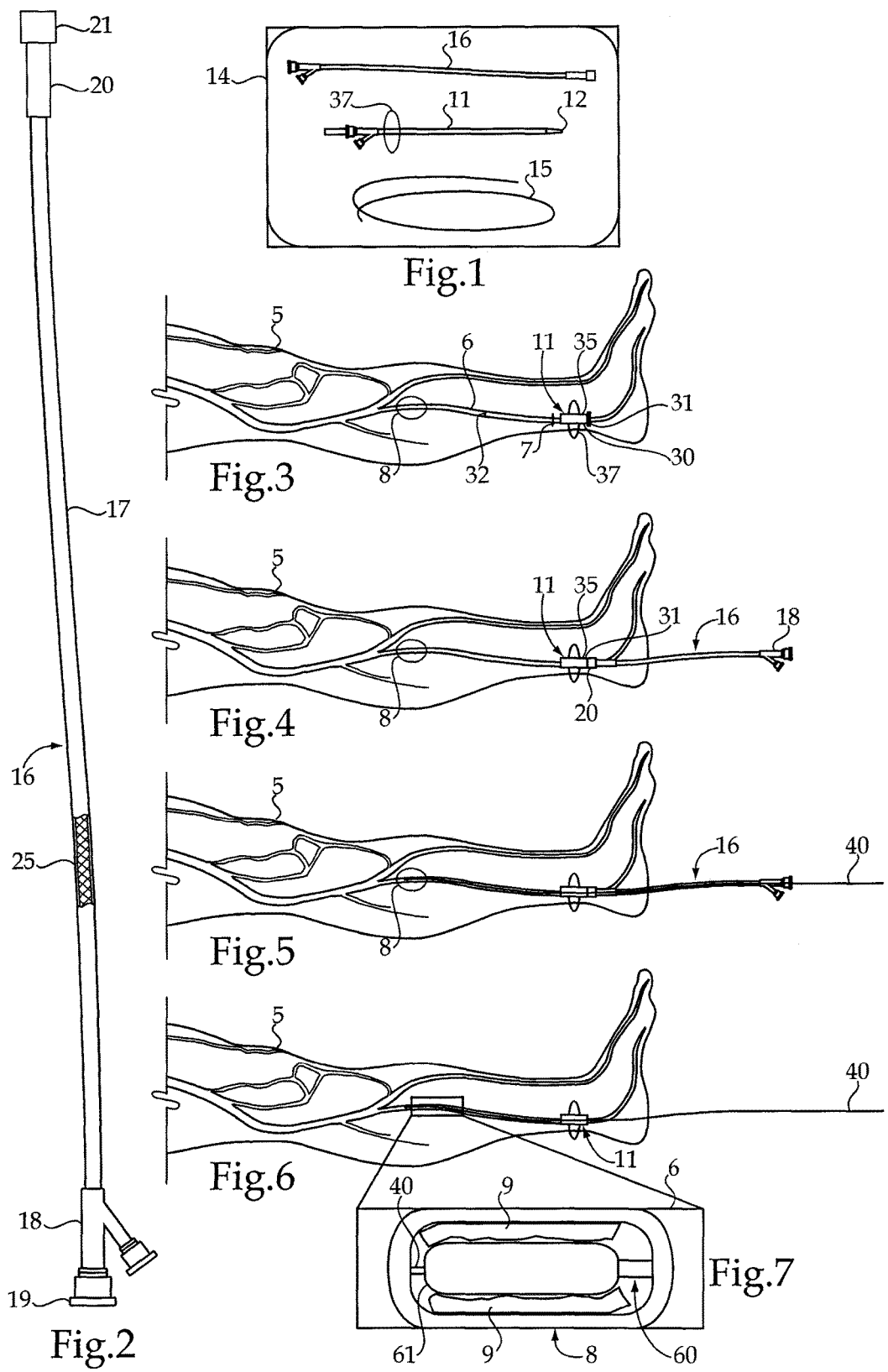

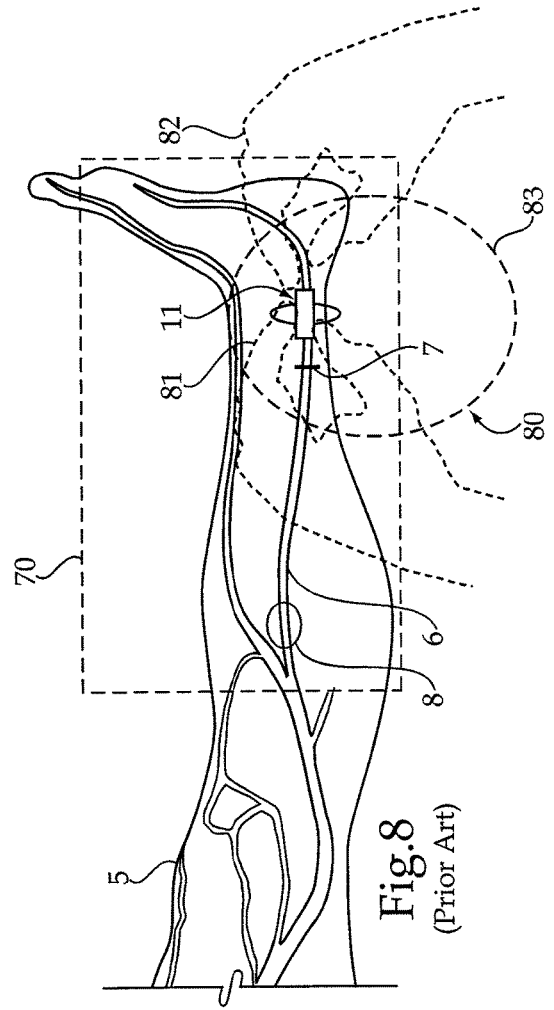
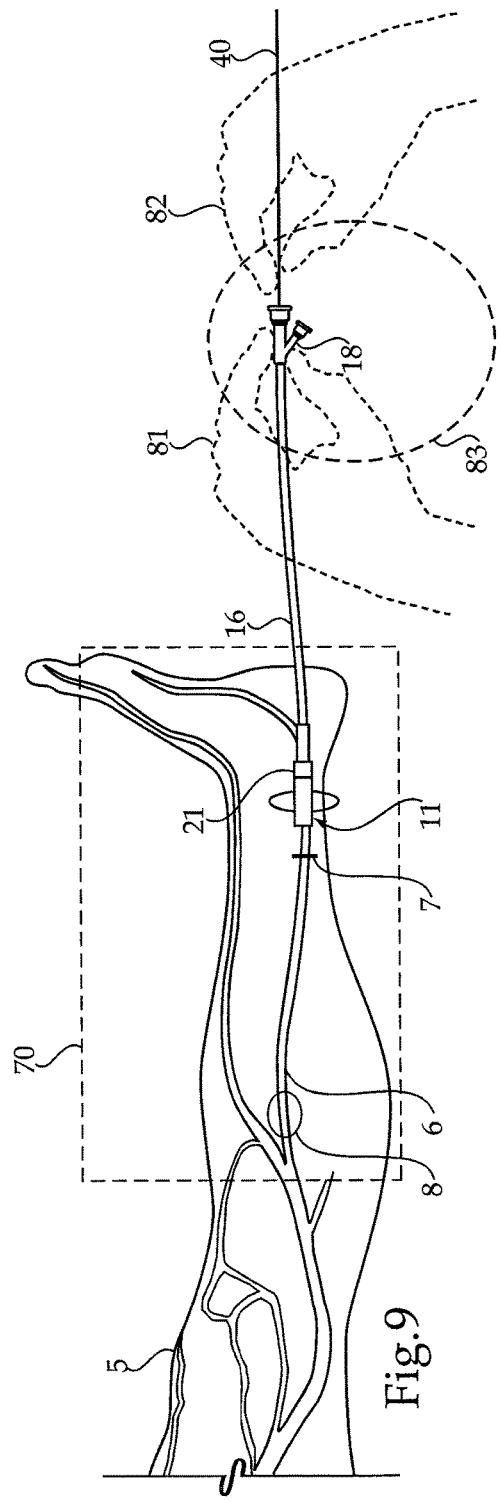
Fig.8 (Prior Art)
Fig.9

INTRODUCER ASSEMBLY EXTENSION AND METHOD OF USE

TECHNICAL FIELD

This disclosure relates generally to the treatment of patients with medical devices through natural passageways of the body, and more particularly to an introducer extension that permits manipulation of a wire guide at a distance away from the puncture entry site.

BACKGROUND

Angioplasty and other surgical techniques that utilize the natural body passageways of a patient to gain access percutaneously to a site to be treated have seen great success. As techniques have improved and medical technology has advanced, these procedures, such as angioplasty, have been performed in ever smaller branches of the circulatory system. For instance, it is now even recognized that angioplasty procedures can be performed in an artery in the lower leg of a patient.

In a typical procedure, access to the patient's circulatory system is gained using the Seldinger technique. In other words, a puncture through the skin and through the wall of a vein or artery is made followed by entry of a small wire guide through the needle. The needle is then withdrawn leaving the wire guide in place. Next, a dilator and introducer are slid over the wire and into the vein or artery. The dilator is then withdrawn leaving only the introducer in place. FIG. 8 shows a prior art procedural step during treatment of a location 8 in an artery 6 of a patient's leg 5 after placement of an introducer 11 through a puncture site 7. With the access to the patient passageway now secured, fluroscopic techniques may be utilized to gain access to a desired treatment location 8, such as a plaque build up in a artery, remote from the puncture entry site 7. This may be accomplished by injecting radiopaque dye into the patient's circulatory system while a physician 80 manipulates a wire guide 40 slid through the introducer 11. While under fluroscopic vision, the wire guide 40 is maneuvered so that its distal end is at or near the area 8 to be treated. Physician 80 will often manipulate wire guide 40 with one hand 82 while holding the introducer 11 in place with their other hand 81. Because of the size of the fluroscopic area footprint 70 and the nearness of the treatment location 8 to the entry site 7, the physician may undergo exposure to direct radiation during this portion of the procedure because their hands 81 and 82 as well as their head 83 may be located within the fluroscopic area 70. After wire guide 40 has been properly positioned, a guide catheter may be slid over the wire guide so that its distal end is at or near the treatment site 8. Next, a balloon dilation catheter may be slid through the guide catheter to the desired treatment location 8. The balloon may be inflated to push back the plaque at the problem location to reopen the passageway for good blood flow. Finally, the balloon catheter is deflated and withdrawn from the patient, followed by withdrawal of the introducer 11 and closure of the entry site 7.

During the fluroscopic portion of the treatment, direct radiation passes through the patient in an area 70 that generally includes the area 8 to be treated along with some of the arteries 6 and passageways that must be traversed in order to gain access to the treatment site 8. However, in some instances, such as gaining access to an artery in the lower leg 5 via an antigrade stick, the access location 7 and the treatment location 8 may be sufficiently close that the exposed proximal end of the introducer 11 and the site 8 to be treated may both lay within the fluroscopic area 70 that experiences direct radiation. While short term exposure to fluroscopy for the patient poses little risk, a physician performing hundreds of these interventions a year will be exposed unnecessarily to direct radiation that may cumulatively result in permanent tissue damage. When performing such a procedure, the physician's 80 hands 81, 82 and eyes (head 83) will temporarily be exposed to direct radiation while manipulating the wire guide 40 to gain access to a treatment site 8. Because of the risks involved with exposure to direct radiation, physicians are generally less inclined to perform procedures that require direct radiation exposure.

The present disclosure is directed toward one or more of the problems set forth above.

SUMMARY OF THE INVENTION

In one aspect, an introducer assembly includes an introducer with a distal segment sized to be received through a puncture site and into a passageway within a patient, and a proximal segment with a fitting having a male luer. An extension includes a flexible tube extending between a first fitting with a female luer, and a second fitting with a male luer. The female luer of the extension is connected to the male luer of the introducer.

In another aspect, a method of positioning a wire guide at a desired location in a passageway of a patient includes positioning a distal segment of an introducer through a puncture site into the passageway of the patient while a proximal segment extends outside the patient. An extension is connected to the proximal segment of the introducer. Radiopaque dye is injected into the passageway. The desired location for treatment and at least a portion of the introducer are positioned in a fluroscopic area while a proximal end of the extension is outside of the fluroscopic area. A wire guide is maneuvered through the extension and the introducer into the passageway, and toward the desired location from a location outside of the fluroscopic area while passing radiation through the fluroscopic area.

In still another aspect, an introducer set includes a dilator mated to an introducer. An extension includes a flexible tube extending between a first fitting with a male luer and a second fitting with a female luer. The length between the male luer and the female luer of the extension being in a range of ten to thirty centimeters. The introducer, the dilator and the extension are sterile and sealed in a peel open package.

BRIEF DESCRIPTION OF THE DRAWINGS

FIG. 1 is a schematic view of a introducer set according to the present disclosure;

FIG. 2 is a side view of an extension according to one aspect of the present disclosure;

FIG. 3 shows a step in a antigrade stick procedure in the lower leg of a patient with an introducer already positioned in the patient;

FIG. 4 is a view similar of FIG. 3, except after an extension according to the present disclosure has been connected to the introducer;

FIG. 5 shows a view similar to that of FIG. 4 after a wire guide has been advanced through the extension and introducer to gain access to a treatment location;

FIG. 6 shows the procedure after the extension has been disconnected from the introducer leaving the wire guide in place;

FIG. 7 is a close up view of the site to be treated via inflation of a balloon catheter;

FIG. 8 is a view of a procedure according to the prior art where the physicians hand and head may be positioned in the fluroscopic area; and FIG. 9 is a view similar to that of FIG. 8, except the physician is manipulating a wire guide to gain access to a treatment location while maintaining their hands and head outside of the fluroscopic area using the extension of the present disclosure.

DETAILED DESCRIPTION

Referring to FIG. 1, an introducer set 10 according to the present disclosure includes items known in the art and sealed in a peal away package 14. These known items may include an introducer 11 that is mated to a dilator 12, and package 14 may also include a relatively short introducer wire guide 15, and maybe even an introducer needle (not shown). Unlike previous introducer sets, introducer set 10 according to the present disclosure also includes an extension 16 with a length in a range of ten to thirty centimeters. Nevertheless, this length may vary, but should be sufficient that a physician can be safely out of the direct radiation zone during a procedure of the type described infra. In any event, the dilator 12 mated to introducer 11 may have a length that is shorter than a combined length of introducer 11 and extension 16. Introducer 11 may include adhesive tabs 37 for securing a proximal fitting 30 of the introducer to skin of a patient.

As used in the present disclosure, an introducer means a short (less than 12 inches) tube constructed primarily from plastic with a fitting on a proximal end and terminating with a blunt distal tip. As used in this disclosure, the term blunt means that the distal tip is unsuitable for creating a puncture through a patients skin, as in a sharp needle. Thus, an introducer according to the present disclosure means something other than a needle. As used in this disclosure, an introducer needle means a needle used with an introducer as defined above.

Referring now to FIG. 2, extension 16 includes a flexible tube 17 extending between a distal fitting 20 with a female luer 21 and a proximal fitting 18 with a male luer 19. Proximal fitting 18 may also include a side port of the type well known in the art. An inner lumen extends between proximal fitting 18 and distal fitting 20. The inner lumen of extension 16 can be manufactured from any suitable medical grade tubing and preferably has a low coefficient of friction inner surface to facilitate the sliding action of a wire guide or the like. Also, the tubing 17, as well as the distal fitting 20, are arranged such that when female luer 21 is mated to the male luer 31 on the proximal segment 35 of introducer 11, a smooth transition between the inner lumen of extension 16 to the inner lumen of introducer 11 is facilitated so that a wire guide passing through both will see a relatively smooth transition.

Referring now to FIGS. 3-7 and 9, an example procedure for treating a plaque build up in a lower leg artery 6 of a patient 5 is illustrated. Nevertheless, those skilled in the art will appreciate that the extension 16 of the present disclosure along with its use may be applicable to a wide variety of patient treatments where the Seldinger access strategy is utilized. FIG. 3 shows a leg 5 of a patient that includes a desired treatment site 8 and an artery 6 that is separated a distance from a puncture access site 7. FIG. 3 shows the procedure after the puncture access has been made to the patient and an introducer 11 has been properly positioned so that a distal segment 32 extends into artery 6 while a proximal segment 35 is positioned outside the patient. If desired, adhesive tabs 37 attached to proximal fitting 30 may be utilized to secure the introducer 11 at a location via attachment to the skin of the patient near the puncture site 7. Next, the extension 16 according to the present disclosure is retrieved from the introducer set 10 of FIG. 1, and the female luer 21 (FIG. 2) of distal fitting 20 is mated to the male luer 31 of introducer 11 as shown in FIG. 4. The physician may chosen to utilize extension 16 in this instance because the physician has determined that fluroscopy is necessary in order to properly position a wire guide at the desired treatment location 8.

The procedure is now ready for the injection of radiopaque dye into patient 5 so that the physician 80 can manipulate a wire guide 40 to the treatment location 8 as best shown in FIG. 9. In particular, a fluroscopic area 70 may enclose the treatment area 8 as well as the puncture entry site 7 and the entire length of introducer 11, including its proximal segment 35. However, with extension 16 attached to introducer 11, the physician 80 may manipulate a wire guide 40 while their hands 81 and 82, as well as their head 83 are located outside of fluroscopic area 70. The physician 80 may grip the proximal fitting 18 of extension 16 with one hand 81 while manipulating a wire guide 40 with their opposing hand 82. The physician 80 will maneuver wire guide 40 through extension 16 and introducer 11, into the artery 6 until the distal end of the wire guide 40 is at or near the desired treatment location 8, as best shown in FIG. 5. After the wire guide 40 has been properly positioned and the radiation has ceased, the physician 80 may chose to disconnect extension 16 and slide the same off the proximal end of wire guide 40 to arrive at a configuration as shown in FIG. 6.

The remainder of the procedure may be somewhat typical. For instance, a guide catheter (not shown) may be slid over wire guide 40 so that its distal tip is at or near the desired treatment location 8. Next, a balloon catheter 60 may be slid through the guide catheter (not shown) so that its balloon 60 is positioned within the plaque obstruction 9 as shown in FIG. 7. The balloon 61 is then inflated to deform the plaque build up toward the walls of artery 6 to better open artery 6 to normal blood flow. Next, the balloon 61 is deflated and the balloon catheter is withdrawn from the patient.

INDUSTRIAL APPLICABILITY

The extension 16 according to the present disclosure finds general applicability to percutaneous procedures for gaining access to a desired treatment location within a passageway of a patient. The present disclosure finds a particular application to those instances where there is a desire to manipulate a wire guide to a desired treatment location from a position distant from the proximal fitting of an introducer. A specific application might be when the introducer is located within a fluroscopic area such that a physician 80 manipulating an associated wire guide 40 would have portions of their body, such as hands 81, 82 and/or head 83 partially or wholly positioned within the fluroscopic area 70 for direct radiation during the wire guide maneuvering step. The extension 16 allows the physician to be located safely outside of the fluroscopic area 70 are while still close enough to the entry site 7 to successfully manipulate and maneuver a wire guide 40 to a desired treatment location 8. Thus, the present disclosure finds specific applicability to antigrade stick procedures in the lower leg of a patient, such as for angioplasty treatment of a lower leg artery.

By conveniently including an extension 16 in an introducer set package 14, the physician 80 retains the option of having the extension 16 readily available for use if desired. On the other hand, because the extension 16 can be made economically at a relatively low cost, the inclusion of extension 16 in introducer set 10 may only add an incremental cost increase to the set 10 while providing the physician with greater options, and possibly permitting the physician to perform certain procedures without exposure to direct radiation. Those skilled in the art will appreciate that introducers 11 according to the present disclosure may have a typical construction made from a suitable medical grade plastic tubing that may or may not include echogenic material, such as hollow glass beads, to facilitate imaging via ultrasound. In addition, the introducer may include radiopaque material imbedded in the medical grade plastic to facilitate imaging under fluroscopy. Finally, the extension and/or the introducer may include some reinforcement, such as a braid and/or coil embedded in the medical grade tubing to facilitate better kink resistance and possibly some torque-ability, if needed.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. An introducer set comprising:
   an introducer;
   a wire guide;
   a dilator mated to the introducer;
   an extension that includes a flexible tube extending between a first end and a second end, and a first fitting with a male luer attached to the first end, and a second fitting with a female luer attached to the second end, and a length between the male luer and the female luer being in a range of ten to thirty centimeters;
   the introducer, the dilator, the wire guide and the extension being sterile and sealed in a peal-open package; and
   wherein the introducer set has an assembled configuration in which the extension is axially connected with the female luer to the introducer and the wire guide extends through both the introducer and the extension.

2. The introducer set of claim 1 wherein the dilator has a length that is shorter than a combined length of the introducer and extension, when the extension is connected to the introducer.

3. The introducer set of claim 2 including an introducer needle in the peal-open package.

4. The introducer set of claim 1 wherein a proximal fitting of the introducer includes adhesive tabs for securing the proximal fitting to skin of a patient.

5. The introducer set of claim 1 wherein the introducer includes a distal segment loaded with an echogenic material and a radiopaque material.

6. The introducer set of claim 1 wherein the flexible tube of the extension includes a kink resistant reinforcement.

7. An introducer set comprising:
   an introducer with a distal segment sized to be received through a puncture site and into a passageway within a patient, and a proximal segment with a fitting having a male luer, and the introducer having a longitudinal axis extending between a proximal end and a distal end;
   a wire guide;
   a dilator mated to the introducer;
   an extension that includes a flexible tube with a longitudinal axis extending between a first fitting with a female luer and a second fitting with a male luer, and a length between the male luer and the female luer being in a range of ten to thirty centimeters;
   the introducer, the dilator, the wire guide and the extension being sterile and sealed in a package; and
   wherein the introducer set has an assembled configuration in which the female luer of the extension is connected to the male luer of the introducer with the longitudinal axis of the introducer, a centerline of the female luer, a centerline of the male luer and the longitudinal axis of the flexible tube are co-linear, and the wire guide extends through the introducer and the extension.

8. The introducer set of claim 7 wherein the dilator has a length that is shorter than a combined length of the introducer and extension, when the extension is connected to the introducer.

9. The introducer set of claim 8 including an introducer needle in the package.

10. The introducer set of claim 7 wherein a proximal fitting of the introducer includes adhesive tabs for securing the proximal fitting to skin of a patient.

11. The introducer set of claim 7 wherein the introducer includes a distal segment loaded with an echogenic material and a radiopaque material.

12. The introducer set of claim 7 wherein the flexible tube of the extension includes a kink resistant reinforcement.

* * * * *